(12) United States Patent
Watkiss et al.

(10) Patent No.: US 12,616,356 B2
(45) Date of Patent: May 5, 2026

(54) ENDOSCOPIC ILLUMINATION SLEEVE

(71) Applicant: KARL STORZ Imaging, Inc., Goleta, CA (US)

(72) Inventors: Kent Watkiss, Florence, MT (US); Jonathan Bormet, Goleta, CA (US); George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 315 days.

(21) Appl. No.: 18/458,981

(22) Filed: Aug. 30, 2023

(65) Prior Publication Data

US 2025/0072723 A1    Mar. 6, 2025

(51) Int. Cl.
*A61B 1/00* (2006.01)
*A61B 1/06* (2006.01)
*A61B 1/07* (2006.01)

(52) U.S. Cl.
CPC ........ *A61B 1/00135* (2013.01); *A61B 1/0638* (2013.01); *A61B 1/0653* (2013.01); *A61B 1/0669* (2013.01); *A61B 1/0684* (2013.01); *A61B 1/07* (2013.01)

(58) Field of Classification Search
None
See application file for complete search history.

(56) References Cited

U.S. PATENT DOCUMENTS

| | | | | |
|---|---|---|---|---|
| 5,406,938 | A * | 4/1995 | Mersch | A61B 1/00096 359/488.01 |
| 5,588,949 | A * | 12/1996 | Taylor | G02B 21/22 600/172 |
| 5,947,958 | A * | 9/1999 | Woodard | A61N 5/0601 606/15 |
| 6,293,910 | B1 * | 9/2001 | Yamakita | A61B 1/0623 600/110 |
| 6,387,044 | B1 * | 5/2002 | Tachibana | A61B 1/00135 600/114 |
| 6,449,006 | B1 * | 9/2002 | Shipp | H04N 13/254 600/101 |
| 6,478,730 | B1 * | 11/2002 | Bala | A61B 1/3132 600/125 |
| 6,692,431 | B2 * | 2/2004 | Kazakevich | A61B 1/07 600/137 |
| 6,761,684 | B1 * | 7/2004 | Speier | A61B 1/00142 600/125 |

(Continued)

*Primary Examiner* — John P Leubecker
(74) *Attorney, Agent, or Firm* — David N. Villalpando; Jacqueline Cohen

(57) ABSTRACT

An endoscopic illumination sleeve includes a housing holding a plurality of LED light sources (LEDs) for providing light to respective light fibers, the housing forming a chamber sized for encircling an endoscope shaft. A flexible sleeve is coupled to the housing and including the light fibers, the flexible sleeve adapted to be placed around the endoscope shaft such that a distal end of the sleeve is positioned toward the distal end of the endoscope shaft and the light fibers extend from the housing to the distal end to illuminate a scene. The flexible sleeve and housing are adapted to be secured around the endoscope in a working position for a medical procedure, and to be removable therefrom. A kit may include multiple sleeves providing different lighting capabilities.

20 Claims, 5 Drawing Sheets

(56)            References Cited

U.S. PATENT DOCUMENTS

| | | | | |
|---|---|---|---|---|
| 6,814,699 | B2 * | 11/2004 | Ross | G02B 23/2461 |
| | | | | 362/555 |
| 7,668,450 | B2 * | 2/2010 | Todd | G03B 37/005 |
| | | | | 396/117 |
| 8,360,968 | B2 * | 1/2013 | Hadani | A61B 1/00135 |
| | | | | 600/178 |
| 8,585,235 | B2 * | 11/2013 | Rockrohr | A61B 17/3462 |
| | | | | 362/190 |
| 12,016,534 | B2 * | 6/2024 | Flower | A61B 1/042 |
| 2002/0013513 | A1 * | 1/2002 | Bala | A61B 1/042 |
| | | | | 600/178 |
| 2002/0193664 | A1 * | 12/2002 | Ross | A61B 1/0607 |
| | | | | 600/179 |
| 2003/0163030 | A1 * | 8/2003 | Arriaga | A61B 1/00181 |
| | | | | 600/182 |
| 2004/0143167 | A1 * | 7/2004 | Branch | A61B 90/30 |
| | | | | 600/212 |
| 2004/0143169 | A1 * | 7/2004 | Branch | A61B 90/36 |
| | | | | 600/245 |
| 2006/0069314 | A1 * | 3/2006 | Farr | A61B 1/0653 |
| | | | | 600/179 |
| 2006/0206007 | A1 * | 9/2006 | Bala | A61B 1/0607 |
| | | | | 600/178 |
| 2006/0211918 | A1 * | 9/2006 | Lieponis | A61B 1/07 |
| | | | | 600/128 |
| 2006/0224045 | A1 * | 10/2006 | Whipple | A61B 90/30 |
| | | | | 600/245 |
| 2007/0270653 | A1 * | 11/2007 | Vayser | A61B 1/00135 |
| | | | | 600/182 |
| 2007/0276191 | A1 * | 11/2007 | Selover | A61B 17/3421 |
| | | | | 606/14 |
| 2008/0208006 | A1 * | 8/2008 | Farr | A61B 1/0676 |
| | | | | 600/178 |
| 2010/0022829 | A1 * | 1/2010 | Irion | A61B 1/00124 |
| | | | | 600/109 |
| 2011/0060184 | A1 * | 3/2011 | Rothberg | A61B 1/0684 |
| | | | | 600/178 |
| 2012/0190990 | A1 * | 7/2012 | Ohzawa | G02B 23/26 |
| | | | | 600/478 |
| 2014/0316206 | A1 * | 10/2014 | Vasan | A61B 1/00105 |
| | | | | 600/199 |
| 2017/0215715 | A1 * | 8/2017 | Harrah | A61B 1/307 |
| 2019/0008551 | A1 * | 1/2019 | Entabi | A61B 17/3415 |
| 2020/0246105 | A1 * | 8/2020 | Levesque | A61B 34/35 |
| 2022/0273167 | A1 * | 9/2022 | Mark | A61B 1/0684 |

* cited by examiner

ENDOSCOPIC ILLUMINATION SLEEVE

BACKGROUND OF THE INVENTION

Field of the Invention

This invention relates to endoscopic illumination, and in particular to a sleeve system for augmenting the illumination of an endoscope as well optionally providing improved sterility.

Description of the Background Art

Endoscopes often include an integrated illumination system for illuminating a scene within the field of view of the scope. This illumination system generally has a fixed set of capabilities, often providing a single type of illumination light and a limited capacity for delivery of illumination.

One known light augmentation system is found in U.S. Pat. No. 5,558,669, which discloses a disposable fiber optic sleeve that can be attached to an endoscope/needle for interocular surgery. The sleeve contains fiber optic bundles. The bundles can theoretically be used for illumination, video transmission and delivery of laser energy. Lenses may be incorporated at the distal ends of the fiber bundles to disperse or focus light. The sleeve is described as being made of a soft, plastic material, and the entire sleeve is described as being about an inch long.

Another known sleeve system is found in U.S. Published Patent Application No. 2018/0172926 A1. This application discloses an elongated, hollow, flexible cylindrical illumination sleeve formed of a resin. This sleeve can be placed over an endoscopic shaft to provide an illumination source at the distal end of the endoscope. The proximal fiber bundle can be coupled with a light source. This publication also suggests the possibility of a transparent end closure to seal illumination end. A single illumination source is coupled to the entire fiber bundle.

SUMMARY OF THE INVENTION

It is a goal of the invention to provide additional illumination capability to an endoscopic system. It is another goal of the invention to provide additional illumination in a way that simplifies and improves the sanitation process for the endoscopic system. It is another goal of the invention to provide additional provide auxiliary illumination and optical filtration means to an existing endoscope. It is another goal of the invention to provide easily interchangeable illumination/filtration options for existing endoscopes. It is another goal of the invention to provide a simplified control interface for an auxiliary illumination system. It is a further goal of the invention to provide a disposable auxiliary illumination capability whereby an endoscope can be protected from contamination.

According to a first aspect of the invention, an endoscopic illumination sleeve includes a housing holding a plurality of LED light sources (LEDs) for providing light to respective light fibers, the housing forming a chamber sized for encircling an endoscope shaft. A flexible sleeve is coupled to the housing and including the light fibers, the flexible sleeve adapted to be placed around the endoscope shaft such that a distal end of the sleeve is positioned toward the distal end of the endoscope shaft and the light fibers extend from the housing to the distal end to illuminate a scene. The flexible sleeve and housing are adapted to be secured around the endoscope in a working position for a medical procedure, and to be removable therefrom.

In some implementations, the flexible sleeve is created as a single use item attachable and detachable from the housing. In some implementations, the flexible sleeve is made of latex or nitrile.

In some implementations at least one of the plurality of LEDs provides light of a different spectrum than at least one of the other LEDs.

In some implementations a first one of light fibers has a first numerical aperture and a second one of the light fibers has a second numerical aperture, different from the first numerical aperture.

In some implementations, the light fibers are glass fiber bundles. In some implementations, the light fibers are plastic optical fibers (POFs). The plastic optical fibers may be constructed with plastic selected for use with a fluorescence imaging (FI); and the flexible sleeve may include a distal faceplate constructed with at least one filter for filtering fluorescence excitation light.

In some implementations, the flexible sleeve includes at least three LEDs with at least one of the LEDs providing light outside of the visible spectrum for FI imaging; and at least another one of the LEDs providing light in the visible spectrum.

In some implementations, the flexible sleeve includes at least three LEDs, and the endoscopic illumination sleeve provides illumination for multi-spectral imaging (MSI), with at least another one of the LEDs provides light in the visible spectrum.

In some implementations, the distal end of the flexible sleeve is constructed not to obstruct a working channel of the endoscope.

In some implementations, the distal end of the flexible sleeve is constructed with elastic material adapted for holding the distal end of the flexible sleeve in a desired position relative to a distal end of endoscope.

In some implementations, the distal end of the flexible sleeve is terminated by faceplate. The faceplate may transparent. The faceplate may include a dichroic filter or a polarization filter. The faceplate may be keyed to align with an endoscope on which the flexible sleeve is placed and includes an opening to allow access a working channel of the endoscope. The faceplate may include one of: an opening or door in the faceplate to access a working channel of the endoscope, or an opening wherein the key comprises a distal extension surrounding the opening on the back side of the faceplate keyed to fit in the working channel of the endoscope. The faceplate may be keyed to align with an endoscope on which the flexible sleeve is placed and includes multiple filter elements to filter respective regions of the faceplate. The faceplate may be an annular element that is positioned, when the flexible sleeve is placed in the working position, along a distal face of the endoscope, with the faceplate including at least one spread lens coupled to at least one of the light fibers.

In some implementations, the endoscopic illumination sleeve includes a wireless transceiver coupled to the LEDs and configured to enable wireless control of the LEDs from an endoscope, camera head, or camera control unit. The endoscopic illumination may also include an identifier configured for communicating at least an identifying code to an endoscope, camera head, or camera control unit for identifying capabilities and properties of the endoscopic illumination sleeve.

In some implementations, the housing includes proximal lenses and/or filters coupled to at least some of the light fibers.

In some implementations, the housing includes a plurality of lenses each focusing light from a respective one of the LEDs onto a respective one of the light fibers.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE VARIOUS EMBODIMENTS

As used herein, elements (e.g., sensors and lenses) that are "optically arranged" in relation to other elements, refers to the elements' position along an optical path shared by first and other elements.

Figure 1:
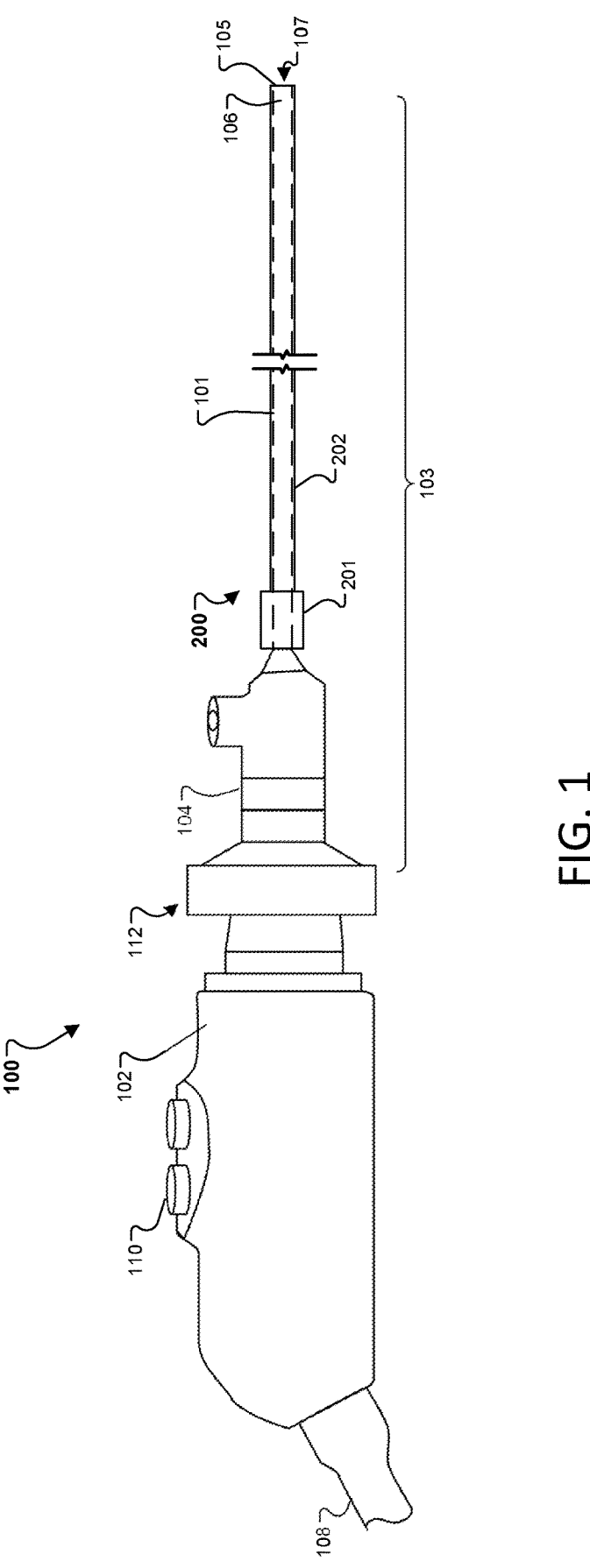
FIG. 1 is a perspective view of an endoscope instrument, including a detachable endoscope connected to a camera head, and an endoscopic illumination sleeve according to an example embodiment.

Referring to FIG. 1, depicted is a perspective view of an endoscopic instrument 100 employing an endoscopic illumination sleeve 200 according to one aspect of the present invention. Instrument 100 generally includes a scope element 103 including an elongated shaft 101, the scope element being in this configuration detachably connected to a camera head 102. The scope 103 can be detachably connected to the camera head 102 by any means known in the art, such as a bayonet connector 112, or alternatively the elements may be parts of a single instrument 100 in which the scope is permanently affixed to a handle element, such as is the case, for example, with video endoscopes and sterile single use (SSU) scopes. Shaft 101 is shown in dashed lines to indicate it is shown inside endoscopic illumination sleeve 200 in the depicted configuration. Shaft 101 extends from a proximal end shown generally at reference numeral 104 connected to camera head 102 to a distal end generally indicated at reference numeral 105. A distal end portion 106 is included at the shaft distal end 105. An objective lens 107, often a wide angle lens, is located at the distal end portion 106, although it is not shown in FIG. 1 due to the scale of the figure. The rigid, elongated shaft 101 generally comprises a relay lens system, such as a series of coupled rod lenses, to transmit an image collected by the objective lens 107 to the proximal 104 portion of the scope 103. The relayed image is then received by the camera head 102. The shown shaft 101 is a rigid implementation, but flexible-shaft implementations are also possible, as well as implementations wherein the image sensor(s) and associated optics are placed in the distal end of the scope 105, and the image information is usually transmitted electronically to the handle portion of the system or, alternatively, may be transmitted wirelessly, and then on to a processor, such as an image processing unit.

Endoscopic illumination sleeve 200 is removable and generally includes a body 201 and a flexible sleeve 202. Endoscopic illumination sleeve 200 is further described below.

Camera head 102 receives electrical operating power through a cable 108 which extends from a proximal end of camera head 102 in this example instrument. This power may be used to operate one or more light sources or, in some embodiments, such as those with distally placed image sensors, other electronic elements mounted within distal portion 105, including one or more electronic image sensors. Also, data signals from such an imaging device may be communicated through appropriate conduits within shaft 101, when image sensors are distally placed, and handle 102 to cable 108. These data signals may be communicated through cable 108 to processing equipment (not shown) which processes the image data and drives one or more video monitors to display the images collected by the instrument 100. Those familiar with endoscopes and borescopes will appreciate that instrument 100 includes a number of additional features such as controls 110 for controlling the operation of the instrument, including, as examples, adjusting the zoom, focus, image rotation, tip deflection, etc. Although data transmission relating to the image sensors will be described further below, the general operation and control of instrument 100 will not be described further herein in order to avoid obscuring the present invention with unnecessary detail. Preferably the designs and techniques herein are employed as improvements to an endoscopic system with image sensors proximally present in the camera head 102 but are also relevant to a distal mounted image sensor arrangement, such as, for example, the endoscopic system described in U.S. Pat. No. 8,814,782 to Hale, et al., issued Aug. 26, 2014, which is hereby incorporated by reference.

Figures 2, 3, 4, 5:
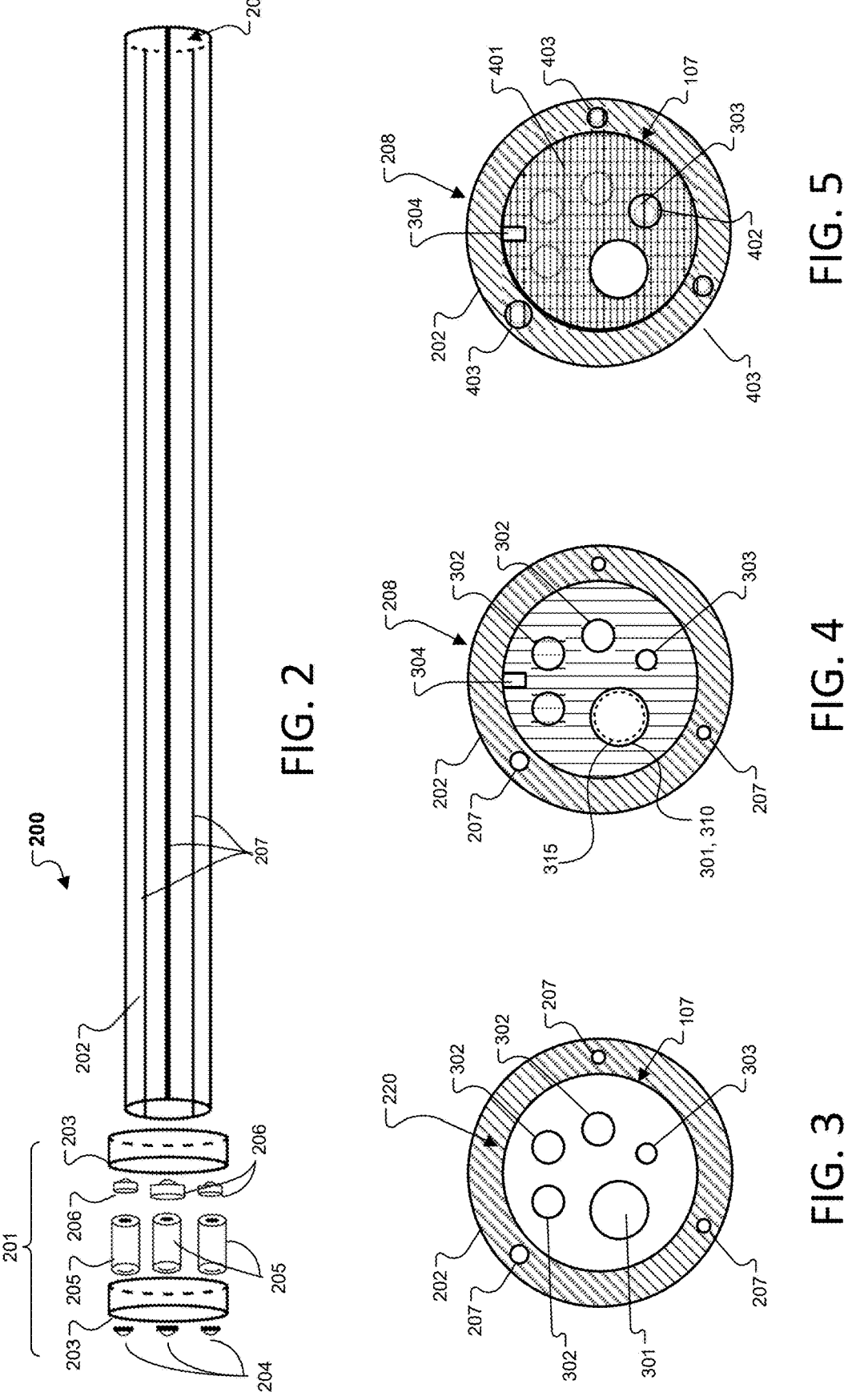
FIG. 2 shows an exploded view of the endoscopic illumination sleeve of FIG. 1.
FIG. 3 shows an end view of a flexible sleeve in the working position on a scope distal end according to an example embodiment.
FIG. 4 shows an end view of a flexible sleeve showing a plan view of a faceplate in the working position on a scope distal end according to an example embodiment.
FIG. 5 shows an end view of another flexible sleeve showing a plan view of a faceplate in the working position on a scope distal end according to another example embodiment.
Figure 8:
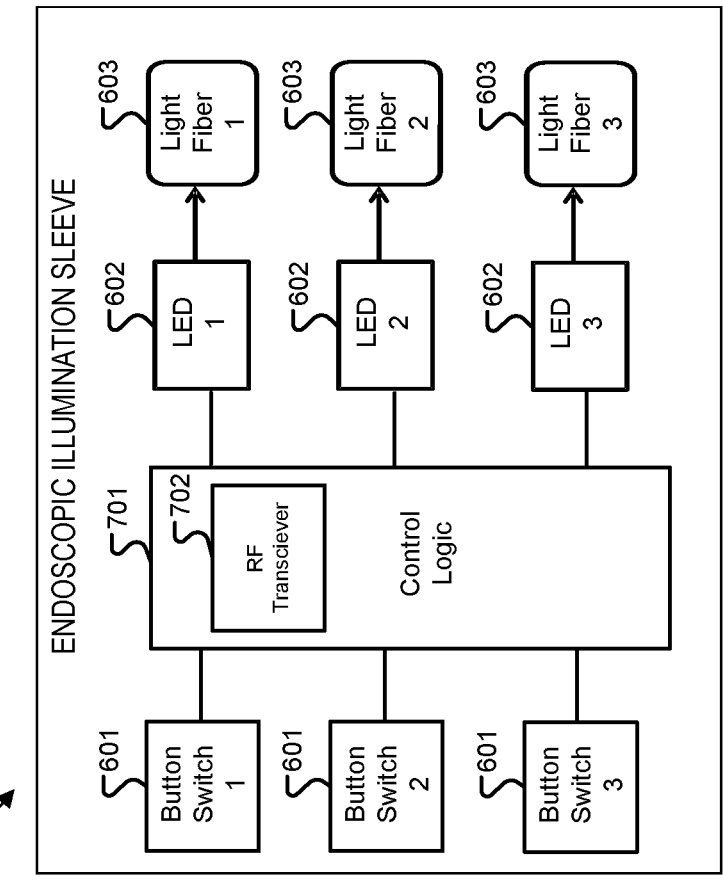
FIG. 8 shows a partial block diagram of a portion of an endoscopic illumination sleeve according to some additional embodiments.
Figure 7:
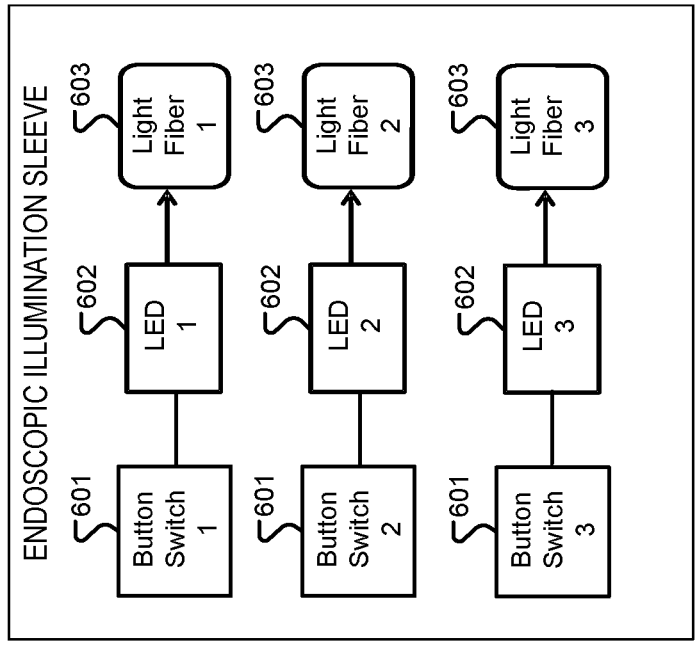
FIG. 7 shows a partial block diagram of a portion of an endoscopic illumination sleeve according to come embodiments.

FIG. 2 shows an exploded view of the endoscopic illumination sleeve 200 of FIG. 1 according to some embodiments. Endoscopic illumination sleeve ("sleeve") 200 includes housing 201 and flexible sleeve 202, which are generally adapted to be secured around the endoscope in a working position for a medical procedure, and to be removable therefrom. Housing 201 includes two body pieces 203, a plurality of control switches 204, a plurality of battery power supplies 205, a plurality of light emitting diodes (LEDs) 206, and various electrical connections (FIG. 7, FIG. 8). Flexible sleeve 202 includes the flexible sleeve itself (202), a plurality of light fibers 207 and, optionally, a distal faceplate 208.

In the assembled configuration, housing 201 forms a chamber sized for encircling an endoscope shaft housing. Housing 201 holds respective LEDs 206 in a position to direct light into respective light fibers 207. A respective lens is included for each LED 206 to focus the light into the proximal end of its respective light fiber 207. Such lenses may be structurally integrated with the LED, may be part of a separate structure such as a lens plate, or may be integrated with the respective light fiber 207.

Flexible sleeve 202 is made of a flexible material such as latex, silicon, or nitrile, and is connected to housing 201. Light fibers 207 are preferably plastic optical fibers (POFs) or glass fiber bundles and are embedded in the material of flexible sleeve 202. Flexible sleeve 202 has a light trans- missive distal end, in this embodiment provided by faceplate 208 which is light transmissive at the distal ends of light fibers 207. Faceplate 208 is joined to flexible sleeve 202 and may include various lenses or filters as further described below. Flexible sleeve 202 adapted to be placed around an endoscope such that a distal end of the sleeve 202 is flush or behind the distal end 106 of the endoscope and light fibers 207 extend from housing 201 to distal end 208 to illuminate a scene. In some embodiments, sleeve 200 is created as a single use item attachable and detachable from the housing, while in other embodiments sleeve 200 is designed for cleaning and re-use. Some embodiments do not include a distal face plate as will be discussed in relation to FIG. 3.

FIG. 3 shows an end view of a flexible sleeve 202 in the working position on a scope distal end 106 according to an example embodiment. The drawing is not shown to scale. Circumferentially around the outside of the scope, a holding material 220 of flexible sleeve 202 is shown with three light fibers 207 visible embedded in the holding material 220. The light fiber 207 on the upper left is depicted as larger than the other two to indicate that it has a larger diameter. The light fibers may have different diameters and/or numerical aper- tures as shown, for example a first light fiber may have first numerical aperture and a second light fiber has a second numerical aperture, different from the first numerical aper- ture.

In this embodiment, holding material 220 extends around the circumference of the distal end 106 of the scope 101. The holding material 220 is generally made of the same material as the sleeve 202 but contains more material in the region and may be of a slightly smaller circumference than that of the sleeve, thereby allowing the distal end of the sleeve 202 to maintain a grip (through material tension) at the distal end 106 of the scope 101. Scopes may contain circumferential grooves or channels near their distal end which may be ideal for receiving the holding material 220. Embodiments such as that shown in FIG. 3 do not occlude the distal face of the scope 101, permitting direct access to the use of a working channel 301, and allows additional illumination as well as improved sterility without affecting illumination sources 302 or imaging objectives 303.

FIG. 4 shows an end view of a flexible sleeve 202 showing a plan view of a faceplate 208 in the working position on a scope distal end 106 according to another example embodiment. The drawing is not shown to scale. Around the outside, the material of flexible sleeve 202 is shown visible through faceplate 208 with three light fibers 207 visible embedded in the material of flexible sleeve 202. The light fiber 207 on the upper left is depicted as larger than the other two because it has a larger numerical diameter. The light fibers may have different diameters and/or numerical apertures, for example a first light fiber may have first numerical aperture and a second light fiber has a second numerical aperture, different from the first numerical aper- ture.

In this embodiment, faceplate 208 extends over the entire circular area shown, to cover both the scope distal end 106 and the distal termination of the flexible material of flexible sleeve 202. Faceplate 208 has an opening 301 for accessing the working channel of the scope, through which instru- ments or working tool tips may be passed. A keyed surface or surfaces 304 is present in faceplate 208, shaped to match a corresponding, inverse keyed surface or surfaces in/on the endoscope distal face to ensure that flexible sleeve 202 is correctly positioned to place opening 301 in position to allow access to the working channel. Such a key may also be useful in positioning various lenses and filters, even in cases where the endoscope does not include a working channel. Opening 301 may include an opening or door 310 in the faceplate to enable or deny access to a working channel of the endoscope. For example, the door may close automatically when there is no tool extending through the working channel, restricting, thereby, any flow of materials from a surgical scene into the working channel. Such an opening 301 may include a surrounding extension of mate- rial, forming, for example, a circular ridge, on the back (proximal) side of the faceplate operating as a key 315 to fit in the working channel of the endoscope. For example, a cylindrical or oval 315 protrusion (depending on the shape of the working channel) of 1 or 2 mm on the back of faceplate 208 which fits into the working channel at its edges.

In some embodiments, faceplate 208 is generally trans- parent. In others, faceplate 208 may be transparent, trans- parent in some areas and filtered in some areas, or filtered with one or more filters in all areas. Various lenses and openings may be embodied in faceplate 208. In this example, the endoscope distal end 106 includes three illu- mination sources 302 and an imaging objective 303, which are covered by the transparent faceplate 208. In other embodiments, elements 302 and 303 may have openings of faceplate 208 positioned in front of them in the working position.

In some embodiments, a transparent faceplate is used rather than openings allowing illumination to pass. In other embodiments, the faceplate may not cover the entire distal face of the endoscope, and instead only cover it partially, for example enough to protect the end of the flexible material, and to support a keying structure as described above. For example, an annular faceplate 208 may cover the distal end of flexible sleeve 202 (the diagonal hatched area of FIG. 4) and provide some structure to at least partially form a keyed opening 304. It should be noted that in some embodiments no key is necessary, for example, in cases where a working channel is not to be accessed and there is no registration required between the face plate and the various positions of the illumination sources 302 and imaging objective 303. Such embodiments enable the sleeve to provide additional illumination to the scene while simultaneously avoiding contamination to the scope, with the further advantage of potentially sealing off a working channel, thereby enabling far simpler sanitization of the scope than one wherein an open working channel is exposed during a procedure.

FIG. 5 shows an end view of another flexible sleeve 202 showing a plan view of a faceplate 208 in the working position on a scope distal end 106 according to another example embodiment. Again, the drawing is not shown to scale. In this embodiment, faceplate 208 includes a number of spread lenses 403 positioned in front of light fibers 207 to spread the illumination light exiting from light fibers 207. Spread lenses 403 are embedded in faceplate 208 or may be a molded as elements of the faceplate or adhered thereto.

Faceplate 208 also includes a selective filter 402 posi- tioned in front of imaging objective 303 when in the working position. In this embodiments, selective filter 402 filters fluorescence excitation light. Faceplate 208 may also include a dichroic filter and/or a polarization filter. Faceplate 208 may include a filter 401 positioned in front of the endoscope light source, or this area may be transparent. Like the faceplate 208 of FIG. 4, the embodiment of FIG. 5 is keyed by keyed opening 304 to align with the endoscope on which the flexible sleeve is placed.

Referring to FIGS. 2-5, in some embodiments, at least one of LEDs 206 and associated light fibers 207 provides light of a different spectrum than at least one of the others. A combination of visible light LEDs and fluorescence imaging (FI) LEDs may be used, or a combination of visible light LEDs and LEDs suitable for photodynamic diagnostics (PDD). In some embodiments, all three of these types of LEDs may be present, or a combination of multiple types of LEDs for different frequencies of fluorescence excitation lighting.

In some other embodiments, the invention is embodied as a kit including multiple endoscopic illumination sleeves 200 with different lighting capabilities, for example any combination of visible, FI, and performing photodynamic diagnostics (PDD) capabilities. For example, a kit may include a first endoscopic illumination sleeve 200 operable to enable an endoscope designed for use in a single imaging mode (such as visible light) to operate, when used in conjunction with an illumination sleeve 200, in a first mode performing FI. The kit also includes a second endoscopic illumination sleeve operable to enable an endoscope to work in a second mode performing PDD. In some embodiments, a process of using such a kit includes installing one of the two endoscopic illumination sleeves 200 in the working position on the endoscope, operating the endoscope using one of the first or second modes to perform a medical or diagnostic procedure, then removing the installed endoscopic illumination sleeve 200 and installing the other endoscopic illumination sleeve 200 and operating the endoscope in the other of the first or second modes to perform another medical or diagnostic procedure. Generally, each endoscopic illumination sleeve 200 also supports visible light imaging with at least one of the LEDs 206 and light fibers 207 providing visible light illumination.

While LEDs 206 are shown integrated into housing 201 in these embodiments, in other embodiments housing 201 may instead include an attachment plug, often referred to in the art as a light post, for coupling to one or more light guides from one or more external light sources. In such embodiments, LEDs 206, control switches 204, and power supplies 205 are not necessary elements, in some embodiments, of housing 201, however in other embodiments both internal LEDs 206 and external illumination sources for the sleeve 202 are possible.

Figure 6:
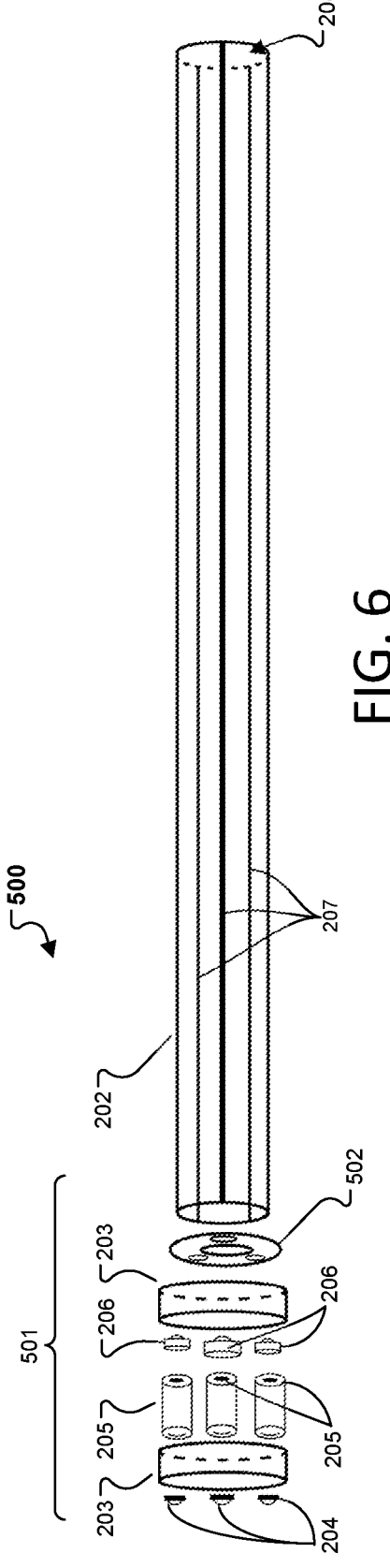
FIG. 6 shows an exploded view of an endoscopic illumination sleeve according to some embodiments.

FIG. 6 shows an exploded view of an endoscopic illumination sleeve 500 according to some embodiments. Generally, endoscopic illumination sleeve ("sleeve") 500 is constructed similarly to sleeve 200 of FIG. 2, with the addition of a filter/lens plate 502 positioned at distal end of housing 201.

Sleeve 500 includes housing 501 and flexible sleeve 202, which are generally adapted to be secured around the endoscope in a working position for a medical procedure, and to be removable therefrom. Housing 201 includes two body pieces 203, a plurality of control switches 204, a plurality of battery power supplies 205, a plurality of light emitting diodes (LEDs) 206, and various electrical connections (FIG. 7, FIG. 8). Flexible sleeve 202 includes the flexible sleeve itself (202), a plurality of light fibers 207 and a distal faceplate 208. Sleeve 500 may include all the variations described above with respect to sleeve 200 and is suitable for use with the same processes and methods described above with respect to sleeve 200.

Filter/lens plate 502 includes suitable lenses for focusing or conditioning the light of LEDs 206 to pass into light fibers 207. Such filter plates 502 maybe interchangeable elements of the housing 501 and may be selected based on the needs of a particular application.

FIG. 7 shows a partial block diagram of an endoscopic illumination sleeve 600 according to come embodiments. The depicted design is suitable for use with the endoscopic illumination sleeve embodiments described herein and for performing the methods and processes described herein. A number of button switches 601 are each connected to control a respective LED 602, powered by power sources such as battery power supplies 205 (FIG. 2). The button inputs for button switches 601 may be positioned at the proximal side of housing 201, as shown in FIG. 2, at a distal face of the housing, or at an outer, circumferential surface. Each of LEDs 602 provide illumination into a respective light fiber 603.

FIG. 8 shows a partial block diagram of an endoscopic illumination sleeve 700 according to some additional embodiments. Endoscopic illumination sleeve 700 generally functions similarly to sleeve 600 but includes a remote control capability provided by radio frequency (RF) transceiver 702 and control logic 701, as well as the ability to reconfigure buttons and advanced control features for LEDs 602. The depicted design is also suitable for use with the endoscopic illumination sleeve embodiments described herein, and for performing the methods and processes described herein. In this embodiment, a number of button switches 601 are each connected to control logic 701 to control a respective LED 602, powered by power sources such as battery power supplies 205 (FIG. 2). Each of LEDs 602 provide illumination into a respective light fiber 603.

Control logic 702 may implement direct control of each LED 602 by button switches 601. Control logic 702 may also implement control features such as duty cycle control (for brightness) or controlling LEDs in a coordinate periodic cycle in which visible light is used in one or more imaging frames, and then FI light is used in one or more subsequent imaging frames.

RF transceiver 702 connects to a similar transceiver in a camera control unit (CCU), illumination controller, or other suitable control unit (not shown) in order to configure and control endoscopic illumination sleeve 700 for use a particular procedure. It provides the ability to control LEDs 602 remotely through a software interface or switch interface at the control unit.

In some embodiments, control logic 701 includes memory for setting illumination modes of LEDs 602. Illumination modes may include a combination of which LEDs 602 are active at the same time, the illumination level of each LED 602, and one or more programmed periodic cycle of LED activation. Such illumination modes may be programmed, activated, and deactivated through RF transceiver 702. In other embodiments, control logic 701 may not include memory or such advanced features and may instead provide the ability to selectively activate each of LEDs 602 at a desired illumination level based on commands received over RF transceiver 702 or button switches 601. In such cases, more advanced features such as periodic cycling may be provided through a stream of commands sent through RF transceiver 702.

Control logic 701 may also activate and deactivate illumination modes using combinations of button presses such as pressing a combination of two of button switches 601 to activate and deactivate a desired illumination mode. While simple button switches are shown in the embodiments of FIG. 7 and FIG. 8, in other embodiments other types of switches may be employed, such as rocker switches allowing "plus" and "minus" illumination level control for each of LEDs 602.

Figure 9:
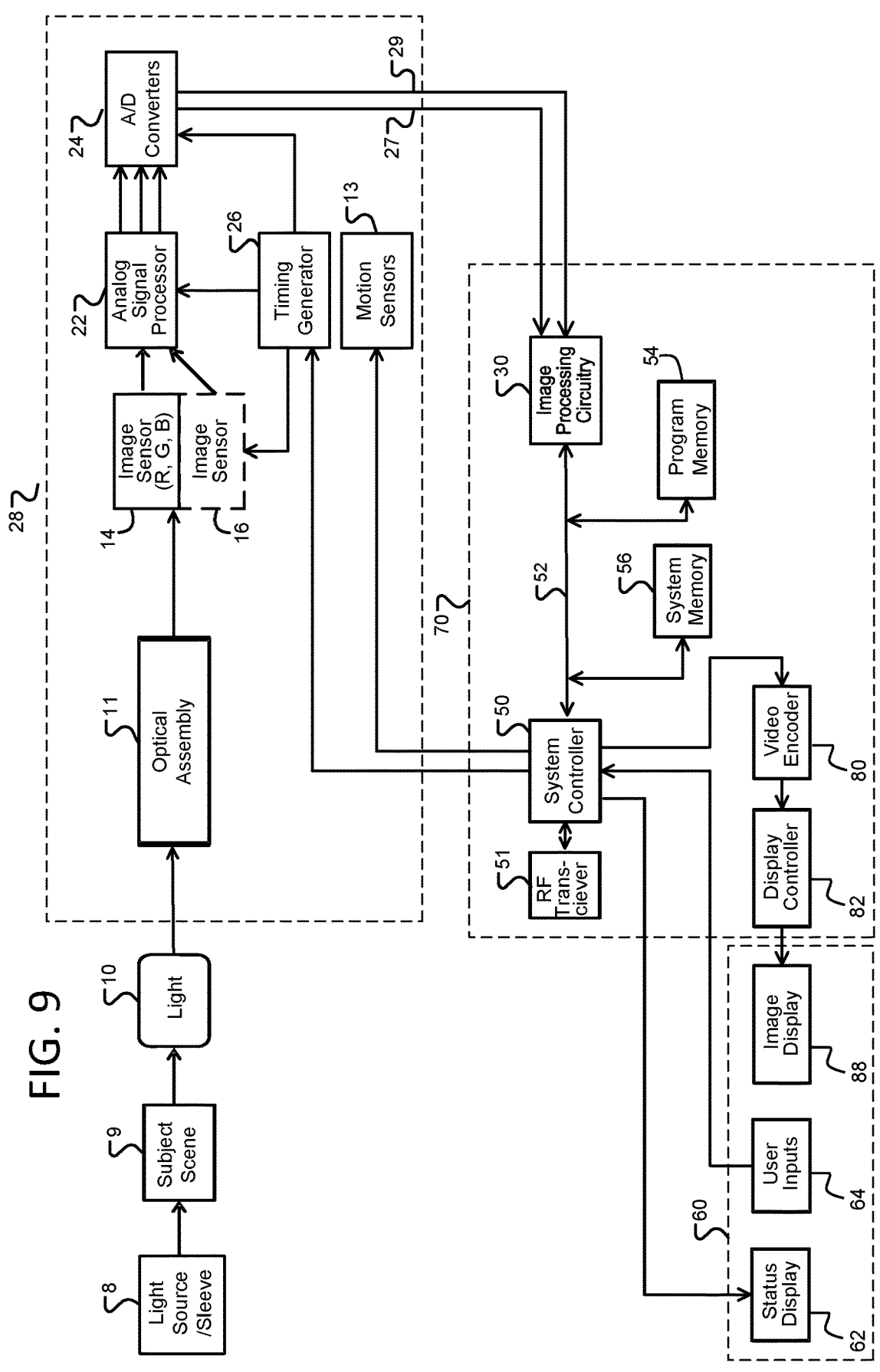
FIG. 9 is a block diagram of an optical instrument system according to an example embodiment.

FIG. 9 is a block diagram of an optical instrument system according to an example embodiment of the present invention. While this example circuit is shown for an endoscope, the present invention is applicable to more than one type of medical scope instrument and is applicable for scope applications that employ image capture at the instrument distal tip or at a camera head, such as endoscopes, borescopes, or exoscopes, for example.

A light source 8 illuminates subject scene 9 and light 10 reflected from (or, alternatively, as in the case of certain fluorescent or digital microscope arrangements, transmitted or emitted by) the subject scene forms an optical image via an optical channel assembly 11, where the light is focused, typically aligned with the scope axis or a desired optical axis, and passed to a proximal side of optical channel assembly 11 onto a single image sensor 14, or in cameras with a separate FI sensor, onto two solid-state image sensors 14 and 16, with image sensor 16 providing capability for FI imaging in a spectrum not supported by imaging sensor 14. Additional image sensors may also be present for other applications such as hyperspectral or 3-D imaging.

In the present invention, optical channel assembly 11 includes a single-channel imaging system and may be constructed according to a large variety of known methods suitable for placement in a scope distal tip or camera head. Image sensors 14 and 16 convert the incident light to an electrical signal by, for example, integrating charge for each picture element (pixel). The image sensors 14 and 16 may be active-pixel type complementary metal oxide semiconductor sensors (CMOS APS) or a charge-coupled devices (CCD), to give just two possible examples. The output analog signal from the image sensors is processed by analog signal processor 22 and applied to analog-to-digital (A/D) converter 24 for digitizing the analog sensor signals. In some versions (typically CMOS designs), the analog signal processing and A/D converters may be integrated into individual sensor models attached to each sensor 14 and 16.

The system's camera 28 generally includes timing generator 26, which produces various clocking signals to select rows and pixels and synchronizes the operation of image sensors 14 and 16, analog signal processor 22, and A/D converter 24. One or more motion sensors 13 such as, for example, an accelerometer, gyro, or magnetometer, may be mounted in the endoscope shaft, tip, or handle to aid in detecting movement, including rotation, of the endoscope. A scope distal tip electronic assembly typically houses image sensors 14 and 16, while the locations of each of analog signal processor 22, the A/D converter 24, and the timing generator 26 may vary, for example in the scope handle 102 or partially integrated into the distal tip electronic assembly. The functional elements of the camera 28 may be fabricated as a single integrated circuit as is commonly done with CMOS image sensors or they may be separately-fabricated integrated circuits.

The system controller 50 controls the overall operation of the image capture device based on a software program stored in program memory 54. This memory can also be used to store user setting selections and other data to be preserved when the camera 28 is turned off. Data connections 27 and 29 carry the digital image data of image sensors 14 and 16, respectively, to image processing circuitry 30, which may be integrated with system controller 50 in some versions or may be a separate programmable logic device or data processor. A data bus 52 provides a pathway for address, data, and control signals. In some variations, data bus 52 may also carry data connections 27 and 29. System controller 50 may communicate with RF transceiver 51 for controlling endoscopic illumination sleeve 700 as some of the embodiments discussed above.

Image processing circuitry 30 performs image processing operations, for example combining partial images from image sensors 14 and 16, performing rotation functions, or other image processing functions desired for specific applications. Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g., on image display 88). The GUI typically includes menus for making various option selections.

Image processing circuitry 30, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Because digital cameras employing endoscopic instruments and related circuitry for signal capture, processing, and correction and for exposure control are well-known, the above description is directed in particular to elements forming part of, or cooperating more directly with, a method and apparatus in accordance with the present invention. Elements not specifically shown or described herein are selected from those known in the art. Certain aspects of the embodiments may be provided in software. Given the system as shown and described according to the invention in the following materials, software not specifically shown, described, or suggested herein that is useful for implementation of the invention is conventional and within the ordinary skill in such arts.

The invention being thus described, it will be obvious that the same may be varied in many ways. Such variations are not to be regarded as a departure from the scope of the invention, and all such modifications as would be obvious to one skilled in the art are intended to be included within the scope of the following claims. For example, reference to an endoscope is intended merely as a representative example application and is not intended to be limiting. Implementations include optical scopes such as exoscopes and bore-scopes. Further, although elements like battery power sources 205, LEDs 206, and sensors 14 and 16 are shown as discreet entities, two or more of said elements may be combined.

Further still, although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

What is claimed is:

1. An endoscopic illumination sleeve comprising:
a housing holding a plurality of LED light sources (LEDs) for providing light to respective light fibers, the housing forming a chamber sized for encircling an endoscope shaft; and
a flexible sleeve coupled to the housing, terminated by a faceplate, and including the light fibers, the flexible sleeve adapted to be placed around the endoscope shaft such that a distal end of the sleeve is positioned toward the distal end of the endoscope shaft and the light fibers extend from the housing to the distal end to illuminate a scene, wherein the flexible sleeve and housing are adapted to be secured around the endoscope in a working position for a medical procedure, and to be removable therefrom; and wherein the faceplate is keyed to align with an endoscope on which the flexible sleeve is placed and includes an opening to allow access to a working channel of the endoscope.

2. The endoscopic illumination sleeve of claim 1 wherein the flexible sleeve is attachable and detachable from the housing.

3. The endoscopic illumination sleeve of claim 1 wherein the flexible sleeve is made of latex or nitrile.

4. The endoscopic illumination sleeve of claim 1 wherein at least one of the plurality of LEDs provides light of a different spectrum than at least one of the other LEDs.

5. The endoscopic illumination sleeve of claim 1 wherein a first one of light fibers has a first numerical aperture and a second one of the light fibers has a second numerical aperture, different from the first numerical aperture.

6. The endoscopic illumination sleeve of claim 1 wherein the light fibers are glass fiber bundles.

7. The endoscopic illumination sleeve of claim 1 wherein the light fibers are plastic optical fibers (POFs).

8. The endoscopic illumination sleeve of claim 1, wherein the faceplate includes at least one filter configured to filter a fluorescence excitation light.

9. The endoscopic illumination sleeve of claim 1, wherein:
the housing includes at least three LEDs; and
at least one of the LEDs provides light outside of the visible spectrum configured for fluorescence imaging (FI); and at least another one of the LEDs provides light in the visible spectrum.

10. The endoscopic illumination sleeve of claim 1 wherein:
the housing includes at least three LEDs;
the endoscopic illumination sleeve is configured to provides illumination for multi-spectral imaging (MSI); and
at least another one of the LEDs provides light in the visible spectrum.

11. The endoscopic illumination sleeve of claim 1, wherein the faceplate is transparent.

12. The endoscopic illumination sleeve of claim 1 wherein the faceplate comprises a dichroic filter.

13. The endoscopic illumination sleeve of claim 1, wherein the faceplate includes one of: an opening or door in the faceplate to access a working channel of the endoscope; and an opening wherein the key comprises a distal extension surrounding the opening on the back side of the faceplate keyed to fit in the working channel of the endoscope.

14. The endoscopic illumination sleeve of claim 1, wherein the faceplate is keyed to align with an endoscope on which the flexible sleeve is placed and includes multiple filter elements to filter respective regions of the faceplate.

15. The endoscopic illumination sleeve of claim 1, wherein:
the faceplate is an annular element that is positioned, when the flexible sleeve is placed in the working position, along a distal face of the endoscope; and
the faceplate includes at least one spread lens coupled to at least one of the light fibers.

16. The endoscopic illumination sleeve of claim 1, further comprising a wireless transceiver coupled to the LEDs and configured to enable wireless control of the LEDs from an endoscope, camera head, or camera control unit.

17. The endoscopic illumination sleeve of claim 16, further comprising an identifier configured for communicating at least an identifying code to an endoscope, camera head, or camera control unit for identifying capabilities and properties of the endoscopic illumination sleeve.

18. The endoscopic illumination sleeve of claim 1, wherein the housing includes proximal lenses and/or filters coupled to at least some of the light fibers.

19. The endoscopic illumination sleeve of claim 1, wherein the housing includes a plurality of lenses each focusing light from a respective one of the LEDs onto a respective one of the light fibers.

20. An endoscopic illumination sleeve comprising:
a housing holding a plurality of LED light sources (LEDs) for providing light to respective light fibers, the housing forming a chamber sized for encircling an endoscope shaft; and
a flexible sleeve coupled to the housing, terminated by a faceplate, and including the light fibers, the flexible sleeve adapted to be placed around the endoscope shaft such that a distal end of the sleeve is positioned toward the distal end of the endoscope shaft and the light fibers extend from the housing to the distal end to illuminate a scene, wherein the flexible sleeve and housing are adapted to be secured around the endoscope in a working position for a medical procedure, and to be removable therefrom, and wherein the faceplate is keyed to align with an endoscope on which the flexible sleeve is placed and includes multiple filter elements to filter respective regions of the faceplate.

* * * * *